United States Patent [19]

McDaniel et al.

[11] Patent Number: 5,087,789
[45] Date of Patent: Feb. 11, 1992

[54] OLEFIN OLIGOMERIZATION

[75] Inventors: Max P. McDaniel; M. Bruce Welch; Marvin M. Johnson, all of Bartlesville, Okla.

[73] Assignee: Phillips Petroleum Company, Bartlesville, Okla.

[21] Appl. No.: 571,684

[22] Filed: Aug. 23, 1990

[51] Int. Cl.$^5$ ................................................ C07C 2/02
[52] U.S. Cl. .................................. 585/525; 585/528
[58] Field of Search .............................. 585/525, 528

[56] References Cited

U.S. PATENT DOCUMENTS

| | | | |
|---|---|---|---|
| 2,694,002 | 11/1954 | Hays | 44/80 |
| 3,375,296 | 3/1968 | Reusser | 260/683.15 |
| 3,463,827 | 8/1969 | Banks | 260/666 |
| 3,620,981 | 11/1971 | Magoon | 252/429 R |
| 3,627,700 | 12/1971 | Zuech | 252/429 B |
| 4,112,011 | 9/1978 | Kolombos | 260/683.15 R |
| 4,364,841 | 12/1982 | McDaniel et al. | 252/430 |
| 4,364,842 | 12/1982 | McDaniel et al. | 252/430 |
| 4,364,854 | 12/1982 | McDaniel et al. | 252/437 |
| 4,364,855 | 12/1982 | McDaniel et al. | 252/437 |
| 4,430,515 | 2/1984 | Bobsein | 585/530 |
| 4,444,962 | 4/1984 | McDaniel et al. | 526/95 |
| 4,444,964 | 4/1984 | McDaniel et al. | 526/105 |
| 4,444,968 | 4/1984 | McDaniel et al. | 526/129 |
| 4,504,638 | 3/1985 | McDaniel et al. | 526/134 |
| 4,826,804 | 5/1989 | Shamshoum | 502/214 |
| 4,835,331 | 5/1989 | Hammershaimb | 585/520 |
| 4,864,068 | 9/1989 | Shamsboum | 585/514 |

Primary Examiner—Curtis R. Davis
Attorney, Agent, or Firm—Richmond, Phillips, Hitchcock & Umphlett

[57] ABSTRACT

In accordance with this invention oligomers are produced by a process comprising contacting propylene, ethylene, or a mixture thereof in a reaction zone, under a reaction temperature within the range of about 130° C. to about 300° C., with a catalyst comprising a chromium component on an aluminophosphate support.

20 Claims, No Drawings

OLEFIN OLIGOMERIZATION

BACKGROUND OF THE INVENTION

This invention relates to the oligomerization of monoolefins.

The preparation of catalysts comprising chromium on an aluminophosphate support is known in the art. Such catalysts are frequently used for olefin polymerization but never before for olefin oligomerization. Providing a catalyst system wherein the catalyst of chromium on aluminophosphate support is used for the production of oligomers would be ideal because of the established methods of production of such catalysts and their commercial availability, and because such catalysts display a high sensitivity to molecular weight regulating agents.

Oligomers have played an increasingly important role in the chemical industry, as exemplified by $\alpha$-olefins processes. Accordingly, oligomers have become important commodity chemicals. Novel processes for oligomerization of olefins are therefore desirable.

SUMMARY OF THE INVENTION

Accordingly it is an object of this invention to provide a novel oligomerization process for the production of oligomers.

It is a further object of this invention to use known chromium catalysts for the production of oligomers.

It is still a further object of this invention to manipulate the reaction zone conditions so that the chromium on aluminophosphate catalyst reacts to produce oligomers from olefins rather than polymers.

In accordance with this invention, a process for producing oligomers comprises contacting at least one monolefin selected from the group consisting of propylene or ethylene in a reaction zone, under a reaction temperature within the range of about 130° C. to about 300° C. with a catalyst comprising a chromium component on an aluminophosphate support and recovering oligomerization products.

DETAILED DESCRIPTION OF THE INVENTION

The chromium on aluminophosphate catalyst can be prepared by any conventional method. Exemplary preparation methods can be found in McDaniel et al., U.S. Pat. No. 4,364,842 and McDaniel et al. U.S. Pat. No. 4,364,855, herein incorporated by reference.

In the description herein the term "hydrogel" is defined as a support containing water. "Xerogel" is a support component which has been dried and is substantially water-free.

The chromium component may be zerovalent, divalent, trivalent, tetravalent, or hexavalent. A suitable chromium compound for use, for example, is an aqueous solution of a water soluble chromium component. Such compounds include, but are not limited to, chromium nitrate, chromium acetate, and chromium trioxide. Alternatively, chromium soluble in an anhydrous solvent such as hydrocarbon can be used. Examples of such anhydrous chromium compounds include, but are not limited to, tertiary butyl chromate, a diarene chromium compound, biscyclopentadienyl chromium II or chromium acetonate.

In selecting a method for combining the chromium with aluminophosphate, the technique recommended depends upon the type of chromium compound selected. If an aqueous solution of chromium is used, the chromium is impregnated onto or coprecipitated with an aluminophosphate base in the form of a hydrogel. The resulting chromium component on the support component is then subjected to activation in an oxygen-containing ambient in a manner conventionally used in the art. Because of economy, the preferred oxygen containing ambient is air, preferably dry air. The activation is carried out at an elevated temperature for about $\frac{1}{2}$ to about 50 hours, preferably about 2 to about 10 hours, at a temperature within the range of about 400° to about 900° C., most preferably at 500° C.-800° C. Under these conditions, a substantial portion of any chromium in the lower valent state is converted to the hexavalent form by this calcination procedure.

If an anhydrous form of chromium is used, the chromium is preferably impregnated onto an aluminophosphate base which is in the form of a xerogel, after the base has been calcined as described above. Temperatures of 150°-800° C., preferably 300°-800° C., more preferably 500° C.-700° C. are suitable. The ambient can be either oxidizing or non-oxidizing but for convenience and economy, an oxygen-containing ambient such as air is preferred. Times of 5 minutes to 24 hours, preferably 0.5 to 10 hours, are suitable for the activation or calcining step.

The chromium component is present in an amount sufficient to give 0.001 to 10, preferably 0.1 to 6 weight percent chromium based on the weight of the aluminophosphate support.

The aluminum and phosphorous components are selected so as to give an atom ratio of phosphorous to aluminum within the range of 0.2:1 to 1:1, preferably 0.6:1 to 0.9:1. Ratios of phosphorous greater than 1 are undesirable because the xerogel tends to be crystalline as opposed to amorphous and because excess phosphorous may deactivate the chromium.

A preferred chromium on aluminophosphate is prepared by coprecipitating an aqueous chromium compound. The chromium component $Cr(NO_3)_3 \cdot 9H_2O$ is combined with a hydrated molten aluminum salt $[Al(NO_3)_3 \cdot 9H_2O]$ and ammonium phosphate monobasic, and thereafter warmed to form a solution. Gelation occurs upon the addition of the concentrated base ammonium hydroxide. After both a water and alcohol bath, the catalyst is dried and a green powder forms. This powder is fluidized with dry air and calcined under a temperature from 400° C. to 600° C. and held for a period of approximately 4-5 hours.

Optionally, a small amount of a boron compound may be included to act as a cocatalyst. It may be combined with the chromium on aluminophosphate in several ways, as discussed in U.S. Pat. No. 4,364,842. The boron compound is generally utilized in an amount so as to give an atom ratio of boron to chromium within a range of 0.5:1 to 15:1, preferably 2:1 to 10:1. The boron compound is preferably a trihydrocarbylboron compond, an alkyl boron alkoxide, or a mixture thereof, more preferably a trialkylborane such as triethylborane, tripropylborane, tributylborane, and the like, with triethyborane being most preferred.

If employed, the boron-containing cocatalyst can either be premixed with the catalyst or added as a separate stream to the oligomerization zone, the latter being preferred.

After the catalyst is prepared, it is preferably pelletized by running a mixture of catalyst and graphite through a pellitizer. The graphite is combined with the catalyst powder to act as a lubricant for the pelletizer. Typically, from 5 weight percent to 10 weight percent graphite is employed, based on the weight of the catalyst. It is not believed that the graphite alters the reaction. Pellets are the desired form of catalyst when the preferred fixed bed operation is employed.

The catalyst system may also employ the catalyst in a slurry of hydrocarbon solvent. Suitable solvents include, but are not limited to, toluene, benzene, chlorobenzene, xylenes, heptane, isobutane, ethylbenzenes, trimethylbenzenes, cumene, and mixtures thereof.

The precise method of establishing contact is not critical. The reaction can be carried out as a batch process or as a continuous process. In a batch process, the olefin-containing gas and catalyst composition can be added in any order to a reaction vessel, which is preferably equipped with mixing/agitating means so as to ensure contact between ingredients. In a continuous process, which is presently preferred, a gas stream comprising at least one $C_2-C_3$ monoolefin is passed through a fixed bed containing the catalyst composition under oligomerization conditions as to produce $C_5-C_{20}$ hydrocarbons.

Any feed which contains propylene, ethylene, or mixtures thereof can be employed. Presently preferred is ethylene. In the reaction zone, the simultaneous contacting of the feed together with the chromium on aluminophosphate catalyst may be carried out under suitable reaction conditions which result in at least partial conversion of said monoolefin to $C_4-C_{20}$ hydrocarbons.

One reaction condition specific to the success of the oligomerization is the temperature of the reaction zone. Oligomerization conditions include a reaction temperature within the range of about 130° to about 300° C., preferably 150° to 300° C., most preferably 230° to 280° C. If temperatures lower than these are employed, polymerization of the olefin feedstock will occur rather than the desired oligomerization.

The amount of catalyst composition useful in the reactions of this invention is that amount sufficient to effect the desired reaction of the olefin feed. Preferably, the flow rate of olefin across the catalyst is in the range of about 0.001 to about 1,000 grams of olefin feed per gram of catalyst per hour, more preferably in the range of 0.01 to 10 grams of olefin feed per gram of catalyst per hour.

Optionally, the catalyst composition may be prereduced in the absence of monomer to attempt to alter the distribution of products obtained. The reduction agent may be selected from carbon monoxide, hydrogen, methane, or the like. Preferably carbon monoxide is employed.

The reduction agent can be employed at temperatures between about 300° to about 500° C. although it is more often employed at temperatures in the range of about 350° to about 450° C. The partial pressure of the reducing gas in the reduction operation can be varied from sub-atmospheric pressures to relatively high pressures. The simplest reducing operation is to utilize a dilute solution of a pure reducing agent at about atmospheric pressure. Usually, a solution of about 10 percent, by volume, carbon monoxide in an inert ambient, such as, for example, nitrogen and/or argon can be used.

The oligomerization reaction is run under conditions of an inert reaction environment. The reaction pressure typically varies from atmospheric pressure up to several thousand psig. Generally it is within the range of 10 to 1,000 psig.

The reaction conditions may optionally include the use of a selectivity modifier such as hydrogen. The catalyst employed in this inventive reaction is very sensitive to hydrogen. By controlling the amount of hydrogen utilized, oligomers of varying molecular weight can be obtained. When hydrogen is used, it is preferably used at partial pressure up to 100 psig.

The relatively low yields of conversion of monoolefins to oligomers is not necessarily indicative of a negative factor. A yield as low as 1 percent or less can still be economically acceptable because conventional techniques involve recycling or circulation of the monoolefin until a substantial conversion is obtained.

Oligomer products are separated and recovered from the reaction mixture by conventional methods such as fractional distillation, selective extraction, adsorption and the like. The reaction diluent, if employed, catalyst and any unreacted monoolefin are recycled for further distillation.

The following example is presented to further illustrate rather than limit the invention.

EXAMPLE I

Catalyst Preparation

A coprecipitate catalyst of aluminum, chromium, and phosphorous was prepared by combining 84.4 g of Al(NO$_3$)$_3$.9H$_2$O (0.225 mole), 10 g Cr(NO$_3$)$_3$.9H$_2$O (0.025 mole), 23.0 g of ammonium phosphate monobasic (0.174 moles), and enough distilled water to reach a final solution volume of 150 ml. The ingredients were then warmed and stirred until a solution was formed. The solution transformed into a gel upon the addition of 65 ml of concentrated ammonium hydroxide (28% NH$_3$). The gel was washed with 4 liters of distilled water three times at 80° C. then filtered and washed three times in 100 percent isopropyl alcohol. The gel was then dried overnight in a vacuum oven at 80° C. and a green powder was formed.

The powder was then pushed through a 35 mesh screen and 12 g was placed in a 2-inch diameter quartz tube containing a porous scintered quartz frit near the bottom. This tube was placed vertically in an electric furnace and dry air was passed up through the frit at about 40 l/hr., causing the catalyst to fluidize. The furnace oven temperature was then increased at about 400° C. per hour until 600° C. was reached, whereupon the catalyst held for 3 hours. The catalyst was then removed from the furnace and transferred under dry nitrogen to a sealed air-tight container.

The catalyst particles had a phosphate to metal ratio of 0.7:1, where the metal was 10 mole percent chromium and 90 mole percent aluminum or 5.4% chromium by weight. Analysis showed the catalyst had 0.232 millimoles of hexavalent chromium per gram of catalyst or 1.21% chromium (VI) by weight.

Before use in the reactor, the catalyst was pelletized into ⅛ inch pellets by running a mixture of catalyst and 6 percent graphite through a pelletizer.

Oligomerization Reaction 20.14 g of pellets were placed into a 14" tubular stainless steel reactor with a ⅜" O.D. The tube was placed in a vertical position inside a furnace and heated to 550° C. for 2 hours while dry air was passed downward over the bed. At the same temperature, the bed was flushed well with argon for 4-5 minutes to remove oxygen, and a very slow flow of CO was introduced for a 30-minute period. The CO was then flushed from the reactor with argon while the temperature was lowered to 250° C.

The feedstock ethylene was introduced at 150 psig flowing downward through the bed at 0.126 l/minute (STP), with the pressure being controlled with a back-pressure regulator. The flow was continued for 1 hour. No liquids were observed, but the effluent gas stream was analyzed by gas chromotography for oligomers. Table I shows results after 30 minutes on stream.

TABLE I

| Gas Chromotography Analysis of Oligomerization Product* | |
|---|---|
| 1-butene | 64.2 |
| unknown between $C_4$-$C_5$ | 4.3 |
| branched hexene | 1.3 |
| 1-hexene | 18.6 |
| double bond isomers $C_6=$ | 1.7 |
| unknown between $C_6$-$C_8$ | 3.0 |
| 1-octene | 2.3 |
| double bond isomers $C_8=$ | .2 |
| unknown between $C_8$-$C_9$ | 4.3 |
| 1-decene | .1 |

*Analysis of gas showed 95.3% of the feedstock ethylene and 4.676% oligmerization product.

That which is claimed is:

1. A process for producing oligomers comprising:
   (a) contacting at least one monoolefin selected from the group consisting of propylene or ethylene in a reaction zone, under a reaction temperature within the range of about 130° C. to about 300° C., with a catalyst comprising a chromium component on an aluminophosphate support; and
   (b) recovering oligomerization products.

2. A process according to claim 1 wherein said reaction temperature is within the range of 150° C. to 300° C.; said chromium component is selected from the group consisting of zerovalent chromium, divalent chromium, trivalent chromium, tetravalent chromium, or hexavalent chromium; said chromium is present in an amount within the range of about 0.001 to about 10 weight percent based on the weight of said aluminophosphate support; and said aluminophosphate support has a phosphorous to aluminum atom ratio within the range of about 0.2:1 to about 1:1.

3. A process according to claim 2 wherein said monoolefin comprises ethylene; said reaction temperature is within the range of 230° C. to 280° C., said chromium is present in an amount within the range of 0.1 to 6 weight percent based on the weight of said aluminophosphate support; said phosphorous to aluminum atom ratio is within the range of about 0.6:1 to 0.9:1.

4. A process according to claim 1 further comprising employing a cocatalyst comprising a boron compound selected from the group consisting of trihydrocarbylboron compounds, alkyl boron alkoxides, or mixtures thereof.

5. A process according to claim 4 wherein said boron compound is a trialkylborane.

6. A process according to claim 5 wherein said trialkylborane is selected from the group consisting of triethylborane, tripropylborane, or tributylborane in an amount sufficient to give an atom ratio of boron to chromium within the range of 0.5:1 to 15:1.

7. A process according to claim 6 wherein said catalyst is present in an amount sufficient to give an atom ratio of boron to chromium within the range of 2:1 to 10:1, said boron compound is triethylborane.

8. A process according to claim 1 further comprising prereducing said catalyst in the presence of a reduction agent selected from the group consisting of carbon monoxide, hydrogen, or methane.

9. A process to claim 2 further comprising prereducing said catalyst in the presence of carbon monoxide.

10. A process according to claim 1 wherein said catalyst has been activated in an oxidizing ambient at a temperature within the range from about 300° to about 800° C. prior to said contacting.

11. A process according to claim 2 further comprising activating said catalyst in air at a temperature within the range of 400° to 600° C. prior to said contacting.

12. A process according to claim 1 further comprising the use of a selectivity modifier.

13. A process according to claim 2 further comprising the use of hydrogen as a selectivity modifier.

14. A process according to claim 1 wherein said reaction zone occurs under slurry conditions.

15. A process according to claim 2 wherein said reaction zone occurs under slurry conditions.

16. A process according to claim 1 wherein said reaction zone occurs under fixed bed conditions.

17. A process according to claim 2 wherein said reaction zone occurs under fixed bed conditions.

18. A process according to claim 9 wherein said catalyst is activated at a temperature of 550° C. to 700° C.; said reaction temperature falls within the range of 250° C.±5° C.; said chromium component catalyst is at least predominantly in the hexavalent state; said catalyst is prepared by combining a source of phosphate ions with a hydrated molten aluminum salt and then neutralizing by mixing with a base to form a coprecipitate; and said reaction occurs in said zone under fixed bed conditions.

19. A process for producing a $C_4$ to $C_{10}$ compound said process comprising, contacting ethylene with a catalyst, said catalyst comprising a chromium component on an aluminophosphate component, under conditions comprising a temperature in the range of about 230° C. to 280° C., to produce said $C_4$ to $C_{10}$ compound.

20. A process according to claim 19 wherein said $C_4$ to $C_{10}$ compound is predominantly 1-butene.

* * * * *